United States Patent [19]

Krupey

[11] Patent Number: 5,976,382
[45] Date of Patent: Nov. 2, 1999

[54] REMOVAL OF PROTEINS FROM AQUEUOS MEDIA BY PRECIPITATION

[75] Inventor: John Krupey, Glen Rock, N.J.

[73] Assignee: LigoChem, Inc., Fairfield, N.J.

[21] Appl. No.: 08/676,668

[22] Filed: Jul. 10, 1996

[51] Int. Cl.⁶ .......................... B01D 15/00; B01D 21/01; C08F 8/30
[52] U.S. Cl. .......................... 210/670; 210/692; 210/710; 210/734; 210/735; 525/327.6; 525/327.8; 525/380; 530/421
[58] Field of Search .................................... 210/670, 692, 210/710, 732, 734, 735; 525/327.6, 327.8, 380, 327.4; 530/421

[56] References Cited

U.S. PATENT DOCUMENTS

| | | | |
|---|---|---|---|
| 5,294,681 | 3/1994 | Krupey | 530/421 |
| 5,453,493 | 9/1995 | Krupey | 530/421 |
| 5,534,597 | 7/1996 | Krupey | 530/421 |

*Primary Examiner*—Ivars Cintins
*Attorney, Agent, or Firm*—Omri M. Behr, Esq.

[57] ABSTRACT

There is provided water insoluble cross-linked polycarboxylic acid having at least two strands in a strand skeleton of the formula:

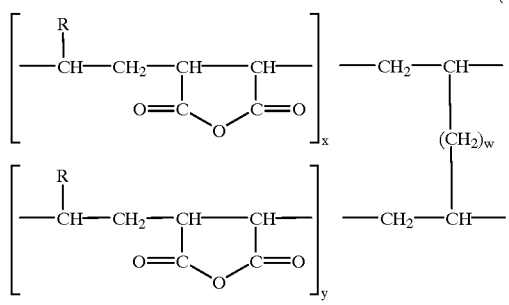

wherein one carbonyl group of at least one maleoyl moiety thereof in each strand is covalently linked to a

—HN.[(H)$_p$(CH)$_2$.(OH)$_m$].NH— moiety to provide the presence therein of at least one cross linked moiety of the formula:

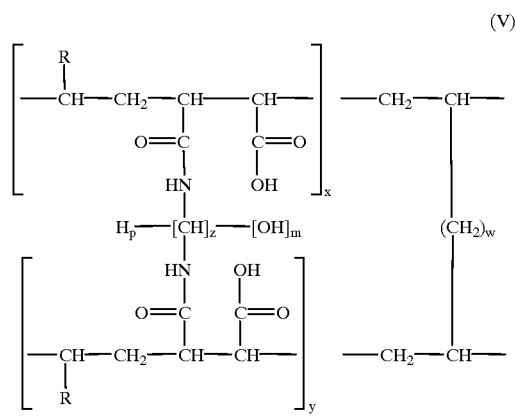

wherein R is hydrogen or lower alkylene or lower alkoxy of 1–4 carbon atoms, or phenyl, x and y are integers, z is an integer of 1–6, p is 0 or an integer up to z–1, m is 0 or an integer up to z, and w is an integer from 2–12. There is disclosed a method of making such polycarboxylic acid as well as methods of utilizing same to remove proteins from aqueous media containing same to provide a matrix. Methods are disclosed for recovering proteins from said matrix without denaturing them and methods for recovering the polycarboxylic acid from said matrix.

50 Claims, 5 Drawing Sheets

REMOVAL OF PROTEINS FROM AQUEUOS MEDIA BY PRECIPITATION

BACKGROUND OF THE INVENTION

1. Field of the Invention

Removal of proteins from aqueous media by precipitation.

2. Discussion of the Prior Art

Proteins have traditionally been removed from aqueous media through use of reagents or heat. Certain solvents (chloroform, urea) denature protein and cause its precipitation. Similarly, raising the electrolyte level of a medium to a high degree by addition of salts also precipitate the protein. Further, heat not only denatures but generally coagulates protein, thus separating it from aqueous media.

There are three major drawbacks to these methods of protein removal. First, the material removed from the medium is not purely protein. Instead, when the medium contains a complex mixture of chemicals as when the medium is a cell lysate, use of these methods may cause removal of other materials in addition to protein. Second, the protein removed by these methods is generally Irreversibly denatured or denaturable only by time consuming procedures such as dialysis. Third, either isolation or purification of the protein traditionally involved use of somewhat toxic solvents (phenol and/or chloroform).

A polymeric material described in U.S. Pat. No. 4,421,653 attempted to overcome these problems. That material, a polyethylene maleic anhydride derivative, cross-linked with diamine, however requires up to 9 volumes in solution, in order to deproteinate a single volume of blood serum. This great excess of the "deproteinizing agent" reveals its low efficiency and renders it unsuitably expensive for commercial processes. Furthermore, this matrix will precipitate proteins in the alkaline range (i.e., pH 10), thus rendering desorption of the desired protein from the matrix very difficult under mild alkaline conditions.

A novel approach to this problem is to be found in applicants earlier U.S. Pat. No. 5,294,681 and its continuation in part application now U.S. Pat. No. 5,453,493. Under certain circumstances however, problems of viscosity arise in the use of these novel compositions. It was therefore considered desirable to seek modifications of the compositions previously disclosed by applicant which avoid these viscosity problems.

SUMMARY OF THE INVENTION

There is provided a group of water insoluble cross-linked polycarboxylic acid compositions obtained by cross-linking a polymer of the formula:

(I)

wherein

R is hydrogen or lower alkylene or lower alkoxy of 1–4 carbon atoms, or phenyl, x and y are integers, w is an integer from 2–12 with an alpha, omega diamino alkane, optionally containing a hydroxy group or hydroxy groups of the formula:

(II)

wherein z is an integer of 1–6, p is 0 or an integer up to z–1, m is 0 or an integer up to z, and hydrolyzing the unreacted anhydride groups,

These cross-linked polycarboxylic or polyhydroxy polycarboxylic acid compositions have a skeleton of the formula

III wherein one carbonyl group of at least one inter-strand maleoyl moiety thereof in each strand is covalently linked to a

(IV)

moiety to provide the presence therein of at least one inter-strand cross linking moiety of the formula:

(IV)

wherein R,x,y,z,p and m are as above to form compound V namely:

(V)

The method disclosed herein of making the cross-linked polycarboxylic acid composition entails cross-linking a polymer of Formula I with an alpha omega diamino alkane of Formula II to yield a compound of formula V.

These cross-linked polycarboxylic or polyhydroxy polycarboxylic acid compositions provide a method of precipitating a protein from an aqueous medium containing the same which comprises adding thereto an effective amount of such a cross-linked polycarboxylic or polyhydroxy polycarboxylic acid composition to provide a protein/polycarboxylic acid composition matrix. Suitably, the amount of polycarboxylic or polyhydroxy polycarboxylic acid composition utilized, by weight, is at least equal to the amount of protein estimated to be contained in the aqueous medium containing same. Furthermore it is desirable that the polycarboxylic acid composition is utilized in an aqueous medium. In this precipitation step, it has been found useful to provide that the concentrations by weight of the protein and of the polycarboxylic acid composition in their respective aqueous media have a ratio of between about 3:1 to about 1:3, most suitably when the concentrations by weight of the protein and of the cross-linked polycarboxylic or polyhydroxy polycarboxylic acid composition in their respective aqueous media are substantially equal.

The actual precipitation process is somewhat pH dependent, within fairly broad ranges, however. Thus, it is desirable that the pH of the cross-linked polycarboxylic acid composition containing medium is between about 3 to about pH 7.5, which after mixture of the components which does not exceed about pH 6.5.

After the precipitation reaction has occurred it is desirable to centrifuge the reaction mixture to recover the matrix therefrom as a pellet.

Separating the protein from the matrix without denaturing said protein may be carried out by treating said matrix with a buffer at about pH 8.6 to about 9.5. Suitably there are used about 1 to about 5 volumes of buffer, at about pH 8.6 to about 9.5, per volume of pellet of the matrix. While the invention is not limited thereto, superior results have been obtained where the buffer is a Tris buffer.

The process is also especially useful for the separation of a nucleic acid from fluids containing both protein and nucleic acid. In such cases the source of the nucleic acids or mixtures thereof is often a cell lysate suspended in aqueous guanidinium thiocyanate or sodium dodecyl sulfate.

Alternatively, one may recover the cross-linked polyhydroxy polycarboxylic acid composition from the matrix to recover it by treating the matrix with an aqueous solution of sodium lauryl sulfate and then, desirably, centrifuging the reaction mixture and recovering the polyhydroxy polycarboxylic acid from or as, the residual pellet.

In this process, in which the protein is denatured, there are used about 1 to about 3 volumes of sodium lauryl sulfate of a concentration of between about 0.5 and about 2% w/w per volume of matrix residual pellet. Thereafter, it is desirable to include the further step of washing the recovered polyhydroxy polycarboxylic acid residue and resuspending it in a buffer where R=methoxy, deionized water suitably at pH 4–4.5 is used.

BRIEF DESCRIPTION OF THE DRAWINGS

The figures are plots of viscosity against time which compare the expansion in water of polymer N and in the presence of various salts with a polymer of the prior art, polymer PA (U.S. Pat. No. 5,453,493—Compound V of Example 2, wherein the polymer is obtained from methyl vinyl ether maleic anhydride copolymer and 1,3-diamino-2-hydroxy propane). Polymer N, a compound of the present invention is obtained from methyl vinyl ether maleic anhydride copolymer cross-linked with 1,9-decadiene and then similarly cross linked with 1,3-diamino-2 hydroxy propane as set forth below.

DESCRIPTION OF THE PREFERRED EMBODIMENTS

The Cross-Linked Polycarboxylic or Polyhydroxy Polycarboxylic Acid Composition

The present invention encompasses a composition of matter formed by cross-linking a polymer of formula I with an alpha, omega diamino alkane suitably a diamino hydroxy alkane of formula II:

wherein m, p, w, and z are as defined above and x and y are integers from 7–10,000.

R is hydrogen or lower alkylene or lower alkoxy of 1–4 carbon atoms, or phenyl.

It is preferred that the symbol R in formula I is methoxy.

Copolymers of methyl vinyl ether/maleic anhydride cross-linked with 1,9 decadiene go under the trade names Stabileze 06 and Stableze Q,M. These two products differ only in particle size and are provided by International Specialty Products (ISP), Bound Brook, N.J. These products are thickeners and they were developed specifically for skin care, hair care and pigmented cosmetics. In contradiction, the present requirements of the present invention are that the final heterogeneously linked product be of low viscosity. In essence, a starting material of high viscosity was converted into a product of very low viscosity.

In Formula II, z is an integer of 1–6, p is 0 or an integer up to z–1, and m is 0 or an integer up to z. It is understood each (CH) group in formula II has either one or no hydroxyl groups attached thereto. The overall cross-linking moiety may have no hydroxyl group and may have up to one hydroxyl group per (CH) group in the cross-linking chain, i.e, up to z hydroxyl groups between the two amide groups.

Alpha, omega diamino alkanes such as those of formula II are commercially available alkanes, suitably diamino alkanes such as 1,3-propylene diamine, 1,6-hexamethylene diamine as well as diamino hydroxy alkanes such as 1,3-diamino-2-hydroxy-propane (Aldrich Chemical Co., Milwaukee, Wis.).

Any anhydride groups remaining in the water insoluble cross-linked polycarboxylic or polyhydroxy polycarboxylic acid are hydrolyzed by alkaline hydrolysis.

In the water insoluble cross-linked polycarboxylic or polyhydroxy polycarboxylic acid composition, the ratio of the initially charged diamino-hydroxy alkane to the initially charged poly(alkylene maleic anhydride) is, suitably, between about $1 \times 10^{-5}$ to $1 \times 10^{-3}$ moles of cross-linker to 1.0 gram of polymer charged.

There is thus formed compound V namely:

[structural formula V]

wherein, most suitably, m=0 or 1, p=3–6 and w=6 and x and y may lie between 7 and 10,000.

Method of Making Cross-Linked Polycarboxylic Acid Composition

The method of making the water insoluble cross-linked polycarboxylic acid composition entails cross-linking a polymer of formula I with an alpha, omega diamino alkane of formula II under strictly anhydrous conditions, and hydrolyzing the unreacted anhydride groups. A volume of alkylene cross-linked poly-(alkylene maleic anhydride) conforming to formula I is added to a reaction vessel. A volume of alpha, omega diamino alkane con-forming to formula II is also added to the reaction vessel. The ratio of the initially charged diamino alkane to the initially charged poly (alkylene maleic anhydride) is, suitably, between about $1 \times 10^{-5}$ to $1 \times 10^{-3}$ moles of cross-linker to 1.0 grams of polymer.

This is performed typically by suspending the polymer of formula I in an anhydrous solvent, suitably acetone and adding a solution of an alpha, omega diamino- or diamino-hydroxy alkane in a similar solvent such as acetone for 1–5 hours followed by stirring for 24–48 hours during which the reaction mixture is allowed to stand at room temperature. The reaction may be carried out at atmospheric pressure at room temperature or elevated temperature. The diamino-alkane cross-links the anhydride groups of the polymer of formula I into carboxy and amide groups. The reaction Is stopped by the addition of water followed by base hydrolysis, suitably with aqueous alkali.

At some time during this hydrolysis step, unreacted anhydride groups are converted into carboxy salt groups and thus removed from the reaction mixture.

It has been the surprising finding that the solutions of the polymers of the present invention are stabilized by alkali metal salts. This stabilization increases in the order $Li^+ < Na^+ < K^+ < Rb^+ < Cs^+$. Potassium and cesium, being readily commercially available are preferred. Any soluble halide is useful, especially chlorides, because of their ready commercial availability. The concentration of alkali metal ion should be adequate to stabilize but not so high as to cause salting out. Thus, it is helpful to prepare a solution of between 0.1% and 10% w/w of polymer in between 0.05 and 0.5 M aqueous alkali metal solution. Most preferred is 1 to 3% w/w of polymer in 0.1–0.3M; most preferably 1% w/w polymer in 0.1 M aqueous potassium or cesium chloride solution.

Method of Protein Removal Using the Water Insoluble Cross-Linked Polyhydroxy Polycarboxylic Acid Composition A further embodiment of the invention is a method of precipitating a protein from an aqueous medium containing the same which comprises adding thereto an effective amount of the cross-linked polyhydroxy polycarboxylic acid composition to provide a protein/polycarboxylic or polyhydroxy polycarboxylic acid composition matrix.

The aqueous medium may be a diluted or undiluted biological fluid containing protein desired to be removed and includes such fluids as whole blood, plasma, sera, lymph, bile, urine, liquid, spinal fluid, sputum, sweat and the like, as well as stool excretions. It is possible also to use fluid preparations of human or other animal tissue such as skeletal muscle, heart, kidney, lungs, brain, including cell culture extracts or milk or microbiological culture fluids or plant extracts. The preferred biological fluids are human blood and bacterial cell lysates.

The water insoluble cross-linked polycarboxylic or polyhydroxy polycarboxylic acid composition may be added to the aqueous medium containing protein in the form of an emulsion, a suspension, a solution or a dry powder.

The ratio of the cross-linked polycarboxylic or polyhydroxy polycarboxylic acid composition to the biological fluid can vary according to the degree of deproteinization desired. The optimum ratio is, however, preferably determined in each case having regard to the concentration of proteins, the nature and the concentration of the substance to be purified, the temperature, the pH value and the ion concentration. The temperature and the pH value are, in principle, not critical. However, the temperature generally lies between 0° and 100° C., preferably above 4° C., but not above 60° C. as substantial irreversible protein denaturation occurs above this temperature.

It is noted that the efficiency of protein precipitation by the cross-linked polycarboxylic or polyhydroxy polycarboxylic acid composition appears to increase at higher temperatures. In other words, less cross-linked polycarboxylic acid composition is required to remove 90% of protein from a sample solution at 60° C. then from an otherwise identical protein solution at 30° C. The efficiency of the composition is greater where there are hydroxy groups on the bridge between the strings, i.e., where the cross-linked agent is a diaminohydroxy alkane.

The pH value in the aqueous medium containing protein, after addition of the water insoluble cross-linked polycarboxylic or polyhydroxy polycarboxylic acid does not exceed about pH 7.5, or preferably about pH 6.5.

The concentrations by weight of the protein and of polyhydroxy polycarboxylic acid and their respective aqueous media suitably have a ratio of between about 3:1 to about 1:3.

The amount of cross-linked polycarboxylic or polyhydroxy polycarboxylic acid composition utilized, by weight is generally at least equal to the amount of protein estimated to be contained in the aqueous medium containing same.

When the water insoluble cross-linked polycarboxylic or polyhydroxy polycarboxylic acid composition is suspended in its own aqueous medium prior to being added to the protein-containing aqueous medium, and R is MeO, the pH of the polycarboxylic or polyhydroxy polycarboxylic acid composition containing medium is between about 3 to about 5, to provided a medium after mixture of the components which does not exceed about pH 6.5.

The degree of the deproteinization of the aqueous medium depends on the density of the reactive groups in the cross-linked polycarboxylic acid composition agent. The density of the reactive groups is not critical for the operability of the invention provided that an adequate quantity thereof is present in order to guarantee the bonding of a sufficient quantity.

Typically, the cross-linked polycarboxylic or polyhydroxy polycarboxylic acid composition agent is added to the biological fluid and after a fixed time (generally 5 to 15 minutes) of intensive contact (e.g. by stirring or inversion followed by standing). The resulting water insoluble phase comprising a matrix of cross-linked polycarboxylic acid composition and protein which has associated with the protein is removed. This removal can be carried out by any conventional method customary for phase separation (e.g. centrifugation, filtration or sedimentation). The removal of the water insoluble phase provides, thereby, a deproteinized supernatant.

Where the removal of the water insoluble phase is by centrifugation, centrifugation should be performed at from about 5 to 100,000 g's for from 0.2 to 10 hours or settling under unit gravity. Ultracentrifugation speeds may be used advantageously because the resulting pellet is so tightly packed no fines are lost when the supernatant is decanted.

The present method of protein removal may also be used to extract a substance, which is precipitated by the cross-linked polycarboxylic acid composition or is precipitated therewith by a suitable treatment such as, for example, by the use of special buffer solutions or other extraction agents such as surfactants. Removal of this substance may be for preparative or analytic purposes. If buffer solutions are used to separate the protein from the matrix, it is accomplished by stirring, grinding and/agitating said matrix with a buffer at about pH 7.0 to about 8.5 for from 10–60 minutes. There are used about 1 to about 5 volumes of buffer, at about pH 7.0 to about 8.5, per volume of pellet of the matrix. The buffer may suitably be Tris buffer. When the matrix is treated with a surfactant extraction agent, (suitably Tween or sodium lauryl sulfate) there may be used about 1 to about 3 volumes of sodium lauryl sulfate of a concentration at between about 0.5 and about 2% w/w per volume of matrix residual pellet.

When one performs the above steps and recovers the water insoluble cross-linked polycarboxylic or polyhydroxy polycarboxylic acid composition from the precipitated matrix, the insoluble polymer may be recovered by (a) washing with water to remove residual surfactant, (b) acidifying the matrix to about pH 1.5, (c) washing the matrix with deionized water until a pH of between 4–4.5 is obtained, and (c) resuspending the polymer in distilled water; final pH 4–4.5.

The method of precipitating protein is especially useful when the protein is present in an aqueous medium with a nucleic acid or mixtures thereof. This is frequently the case when the source of nucleic acid or mixtures thereof is a cell lysate suspended in aqueous guanidium thiocyanate.

The deproteinized supernatant (the deproteinized fluid remaining behind after deproteinization) can be further processed in any manner. For preparative purposes (e.g. for the purification of peptides, glycoproteins, steroids, lipoids, nucleic acids, enzymes, hormones, vitamins, viruses, polysaccharides or alkaloids) further purification steps can, for example, be carried out. In this case, there are suitable, in particular, chromatography (e.g. ion exchange, Sephadex, affinity or adsorption chromatography), filtration, (e.g. ultrafiltration), electrophoresis (e.g. block, disc or carrier-free electrophoresis), isoelectric focusing and selective precipitation.

Without in any way restricting the scope of present invention, Applicant wishes to state his understanding of the present invention, namely the mechanism by which the cross-linked polycarboxylic or polyhydroxy polycarboxylic acid composition removes protein from an aqueous medium. Precipitability is a function of solubility in an aqueous medium. Solubility in turn is a function at least in part of the degree of a protein's hydrophobicity. All proteins have at least some hydrophobic portions of their surface exposed to the aqueous medium. Applicant believes his cross-linked polycarboxylic or polyhydroxy polycarboxylic acid composition permits the hydrophobic portions of different protein molecules to approach one another and aggregate to such a degree that the proteins eventually precipitate. (This appears to be corroborated by the increased protein removal efficiency of the cross-linked polycarboxylic or polyhydroxy polycarboxylic acid composition from solutions at higher temperatures. By contrast, where protein precipitation is caused by other phenomena, e.g., association/dissociation, protein precipitation is seen to fall off as temperature rises).

Before this can happen, the cross-linked polycarboxylic or polyhydroxy polycarboxylic acid composition associates with one or more protein molecules by non-covalent interaction, such as electrical charge attraction. (The cross-linked polycarboxylic or polyhydroxy polycarboxylic acid composition has numerous negative charges which can interact with the partial positive charges present in several points in all protein molecules, e.g. at arginine residues). The local ordering of water imposed by the surface hydrophobic groups is thermo-dynamically unfavored. Bound water may be released when these hydro-phobic groups which are apolar, interact with one another and aggregate. Thus, when two or more proteins which have interacted with the flexible cross-linked polycarboxylic or polyhydroxy polycarboxylic acid composition like beads on a string, the composition-string can then enfold such apolar portions of different protein-beads may aggregate. When the number or size of aggregated protein molecules is large enough, the protein-composition complex precipitates.

The following examples are meant to illustrate the present invention and do not restrict the invention in any respect.

EXAMPLE 1

Preparation of a Water-insoluble Polymer V(a)
Preparation of Polymer 3.0 grams 0.033 moles of 1,3 diamino 2 hydroxy propane were dissolved in 1.0 L of acetone contained in a 2.0 L (acetone) dried glass container. Anhydrous conditions prevailed at all times.

60 g of methyl vinyl ether maleic anhydride cross-liked with 1.9 decadiene (Stabilize 0 6) were dissolved in 1 L of acetone contained in a 5 L reaction flask, and stirred for 30 minutes using a stir setting of 4.5. (This polymer is insoluble in acetone). The cross linker was delivered into the reaction flask at a flow rate of 370 ml/hour using an FMI metering pump (pump setting 4). The reaction proceeded for 48 hours or more at room temperature.

After the reaction period, 2 L of tap water was added to the reaction mixture while stirring. The contents transferred to four 1 L centrifuge bottles and spun at 3000 g for 10 minutes. The supernatant transferred to a 20 L plastic container and placed in a fume hood. The pellet was dispersed in a volume of water equal to the volume of the pellet and then homogenized using a Gifford wood-homogenizer for 30 seconds at a setting of 60. The volume of the homogenate was adjusted to 2.5 L with water. While stirring with a magnetic stirrer, 2.5 L of a solution of 0.2 N sodium hydroxide was added, stirred for 15 minutes and centrifuged at 3000×g for 10 minutes. The pellet was extracted with 4 L of water, dispersed and centrifuged again. This washing procedure was repeated two more times.

The pellet was dispersed in a volume of distilled water equal to the volume of the pellet, stirred with a magnetic stirrer and the pH of the homogenate adjusted to 1.5 by the addition of 4N HCl. After centrifuging the supernatant was discarded. The pellet was washed with distilled water and centrifuged again a nd the washing procedure repeated until the pH of the supernatant reached 5.0–5.5. There is thus provided a polymer of Formula V(a) wherein w=6 and R is methoxy.

Polycarboxylic or polyhydroxy polycarboxylic acid compositions having a cross linking moiety with two carbon atoms may be formed according to the above steps, except that the 1,3-diamino-2-hydroxypropane is replaced with a diamino-hydroxyethane, such as 1,2-diamino-1-hydroxyethane. Polyhydroxy poly-carboxylic acid compositions in which the cross linking moiety has multiple hydroxyl groups may be formed according to the above steps by replacing the 1,3-diamino-2-hydroxy propane with 1,2-diamino-1,2-dihydroxyethane.

Polycarboxylic or polyhydroxy polycarboxylic acid compositions having a cross linking moiety with three carbon atoms having multiple hydroxyl groups may be formed according to the above steps, except that the 1,3-diamino-2-hydroxypropane is replaced with a 1,3-diamino-di- or 1,3-diamino-tri-hydroxypropane such as 1,3-diamino-1,2-dihydroxypropane or 1,3-diamino-1,2,3-dihydroxypropane.

Polycarboxylic or polyhydroxy polycarboxylic acid compositions having a cross linking moiety with four carbon atoms may be formed according to the above steps, except that the 1,3-diamino-2-hydroxypropane is replaced with an alpha, omega-diamino-mono-hydroxy-n-butane, such as 1,4-diamino-3-hydroxybutane or 1,4-diamino-1-hydroxy-butane. Polyhydroxy polycar-boxylic acid compositions in which the cross linking moiety has more than one hydroxyl group may be formed by the above steps, except the alpha, omega-diamino-mono-hydroxy-n-butane is replaced with a 1,4-diamino-di-, 1,4-diamino-tri- or 1,4-diamino-tetra-hydroxybutane, such as 1,4-diamino-2,3-dihydroxybutane or 1,4-diamino-1-2-dihydroxybutane; 1,4-diamino-1,2,3-trihydroxybutane; and 1,4-diamino-1,2,3,4-tetrahydroxybutane.

EXAMPLE 2

Preparation of Polymer V(b) Using a Deoxyaliphatic Diamine (i.e., m=0)

3.66 g. of 1,3 propylene diamine was mixed with 1.0 L acetone in a 3 L dry glass container. Anhydrous conditions prevailed at all times.

60 g of methyl vinyl ether maleic anhydride was cross-linked with 1,9 decadiene (Stabileze 06) in 1 L of acetone contained in a 5 L reaction flask and stirred for 30 minutes using a stir setting of 4.5. (This polymer was insoluble in acetone). The cross-linking reagent was delivered into the reaction flask at a flow rate of 370 ml/hr (pump setting 4). The reaction proceeded for 48 hours or more at room temperature.

After the reaction period, 2 L of tap water was added to the reaction mixture while stirring. The contents was transferred to four 1 L centrifuge bottles and spun at 3000×g for 10 minutes. The supernatant transferred to a 20 L plastic container and placed in a fume hood. The pellet was dispersed in a volume of water equal to the volume of the pellet and homogenized using a Gifford-homogenizer for 30 seconds at a setting of 60. The volume of homogenate was adjusted to 2.5 L with water. With a magnetic stirrer, 2.5 L of a solution of 0.2 N sodium hydroxide was added and stirred for 15 minutes and centrifuged at 3000×g for 10 minutes. The pellet was treated with 4 L of water, dispersed and centrifuged again. This washing procedure was repeated two more times.

The pellet was dispersed in a volume of distilled water equal to the volume of the pellet, stirred with a magnetic stirrer and the pH of the homogenate adjusted to 1.5 by the addition of 4 N HCl, centrifuged and the supernatant discarded. The supernatant was washed with distilled water and centrifuged; the washing procedure repeated until the pH of the supernatant reached 5.0–5.5.

EXAMPLE 3

The principle polyhydroxy polycarboxylic composition made according to Example 1 (V)(polymer N) is evaluated for its ability to precipitate the diverse materials listed in Table 1 below.

All the materials listed in Table 1 (from human serum albumin through plasmid DNA) are obtained in powder or particulate form from the Sigma Chemical Company, St. Louis, Mo.

Bovine serum albumin (BSA) is dissolved in 0.01 M sodium phosphate buffered 0.9% saline, having a pH 7.3–7.5 at a concentration of 33 mg/ml. (The remaining compounds; bovine immuno globulins through glycoproteins are similarly dissolved in an identical phosphate buffered saline at the concentrations indicated in Table 1.

A 1% weight/weight solution of the polyhydroxy polycarboxylic acid composition made in Example 1 (polymer N), as well as the polymer (V) of Example 2 of U.S. Pat. No. 5,4543,493 (polymer PA) is also made using the sodium phosphate buffered saline solution.

One volume of the cross-linked polyhydroxy polycarboxylic acid composition solution ("deproteinizing agent") is combined with equal volumes of the sample solution. Each combination of solutions is mixed by inversion then allowed to stand at room temperature for 10 minutes. Each solution is then centrifuged at 2,000×G for 10 minutes to remove the protein-polyhydroxy polycarboxylic acid composition matrix. The percent of protein removal from each remaining supernatant is measured by ultraviolet absorption (at 280 nm) or colorimetric determination (using the "BCA Protein Assay Reagent" from the Pierce Company, Rockville, Ill.). The percentage of protein removal ("% Removal") is indicated in Table 1.

The proteins bovine serum albumin, bovine immuno globulins and hemoglobin are all removed at levels of 90% or above by the cross-linked polyhydroxy polycarboxylic acid composition. These proteins have uniformly low levels of carbohydrate associated with them. By contrast, alpha 1 acid glycoprotein has substantial amounts of carbohydrate and therefore inferior "percent removal". Finally, as is seen with the DNA sample in Table I, non-proteinaceous materials are hardly precipitated at all by the cross-linked polyhydroxy polycarboxylic acid composition.

TABLE 1

| Sample | Conc. mg/ml | % Removal of Material using Polymer N in a 1:1 Polymer to Sample Ratio | % Removal of Material using Polymer PA in a 1:1 Polymer to Sample Ratio |
|---|---|---|---|
| Reactive Components | | | |
| Bovine Serum Albumin | 33 | 98 | 73.3 |
| Bovine Immuno-globulin | 25 | 95.2 | 78.8 |
| Hemoglobin | 10 | 97.9 | 90.2 |
| Unreactive Components | | | |
| Calf thymus DNA | 1 | <1 | <1 |
| Alpha I Acid Glycoprotein | 1 | 6.2 | 4.1 |

The protein binding data clearly demonstrated that polymer N had a higher protein binding capacity than polymer PA. The effect on unreactive components appears to be similar to that of polymer PA.

EXAMPLE 4

Protein Binding Capacity of Polymer N in the Presence of Anionic and Neutral Surfactants Solutions of BSA were prepared at a concentration of 33 milligrams per milliliter in phosphate buffered saline pH 7.3 and containing either (a) 1.0% w/v Tween 80 or 1.0% w/v sodium lauryl sulfate (SDS) respectively. A 1.0% weight/weight suspension of polymer N dispersed in water was employed. One volume of polymer suspension and one volume of the protein solution containing he respective surfactants were employed in this study. Each combination of protein solution and polymer suspension were vortexed, allowed to stand at room temperature for 10 minutes and centrifuged at 2000×g for 10 minutes. The supernatants were removed and analyzed for protein using UV absorption at 280 nanometers.

The extent of protein removal from the BSA-SDS solution and the BSA-Tween 80, solution was greater than 99%.

EXAMPLE 5

Protein Binding Capacity of Polymer N Cross-Linked with a Deoxyaliphatic Diamine Spacer (i.e., m is equal to zero)

Compound (Vb), i.e., the analogue of Polymer N (1.0% w/w), cross-linked with propylene diamine (polymer NB) and Polymer PA (the old polymer at 1.0% w/w) were compared with regard to protein binding capacity 1 milliliter of each of the suspensions were added to separate tubes containing 1 milliliter of BSA (33 mg/ml, phosphate buffered saline pH 7.3).

The extent of protein removal was 83% for polymer NB (m=0) and 73.5% for the old (polymer PA).

It is interesting to note that the deoxy form of polymer NB (m=0) is less reactive than the polymer N which has a hydroxyl on the aliphatic spacer (m=1). Polymer N (m=1) was shown to remove 98% of the BSA (33 mg/ml original concentration).

EXAMPLE 6

In order to determine the effect of temperature as well as ionic environment on the stability of polymers N and PA, experiments were conducted at 45° C. in water and in the presence of solutions containing chloride salts of the Group I elements. These were water (the polymers were in their form with H⁺ constituting the counterion), 0.1 M LiCl, 0.1 M NaCl, 0.1 M KCl, and 0.1 M CsCl.

All experiments were performed using a 1.0 w/w % of polymer N and polymer PA respectively. Suspensions of the polymers were centrifuged at 3000×g for 10 minutes after which time the polymer gel:liquid volumes were adjusted to yield 1 volume of the gel to 4 volumes of free liquid.

The contents of the tubes were mixed and placed in an incubator at 45° C. The tubes were taken out of the incubator at 24 hour intervals, centrifuged and the gel volume to free liquid volume ratio was recorded. This ratio increased with incubation time and is an indicator of increasing viscosity.

Figure 1:
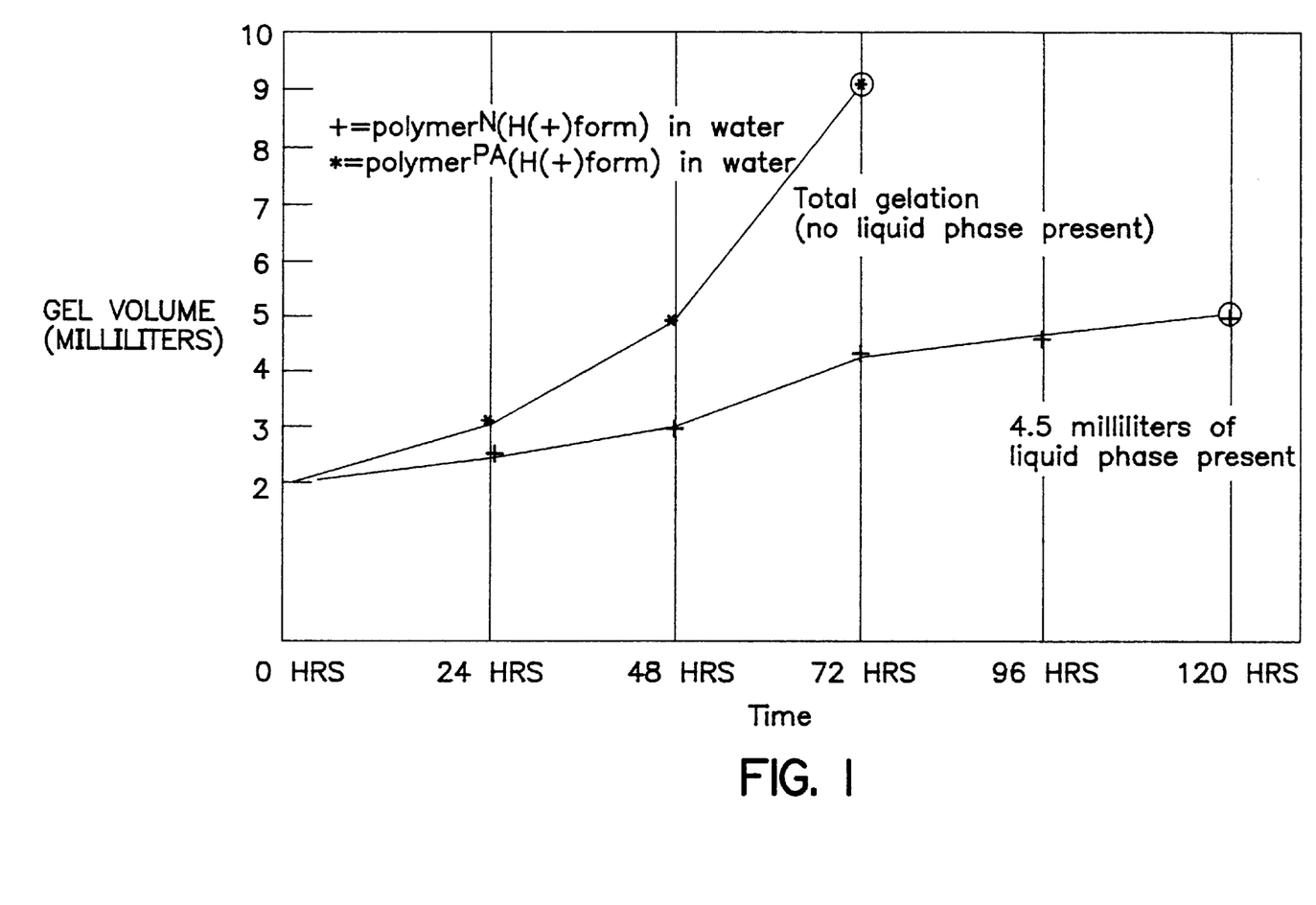
FIG. 1 is an experiment in water.
Figure 2:
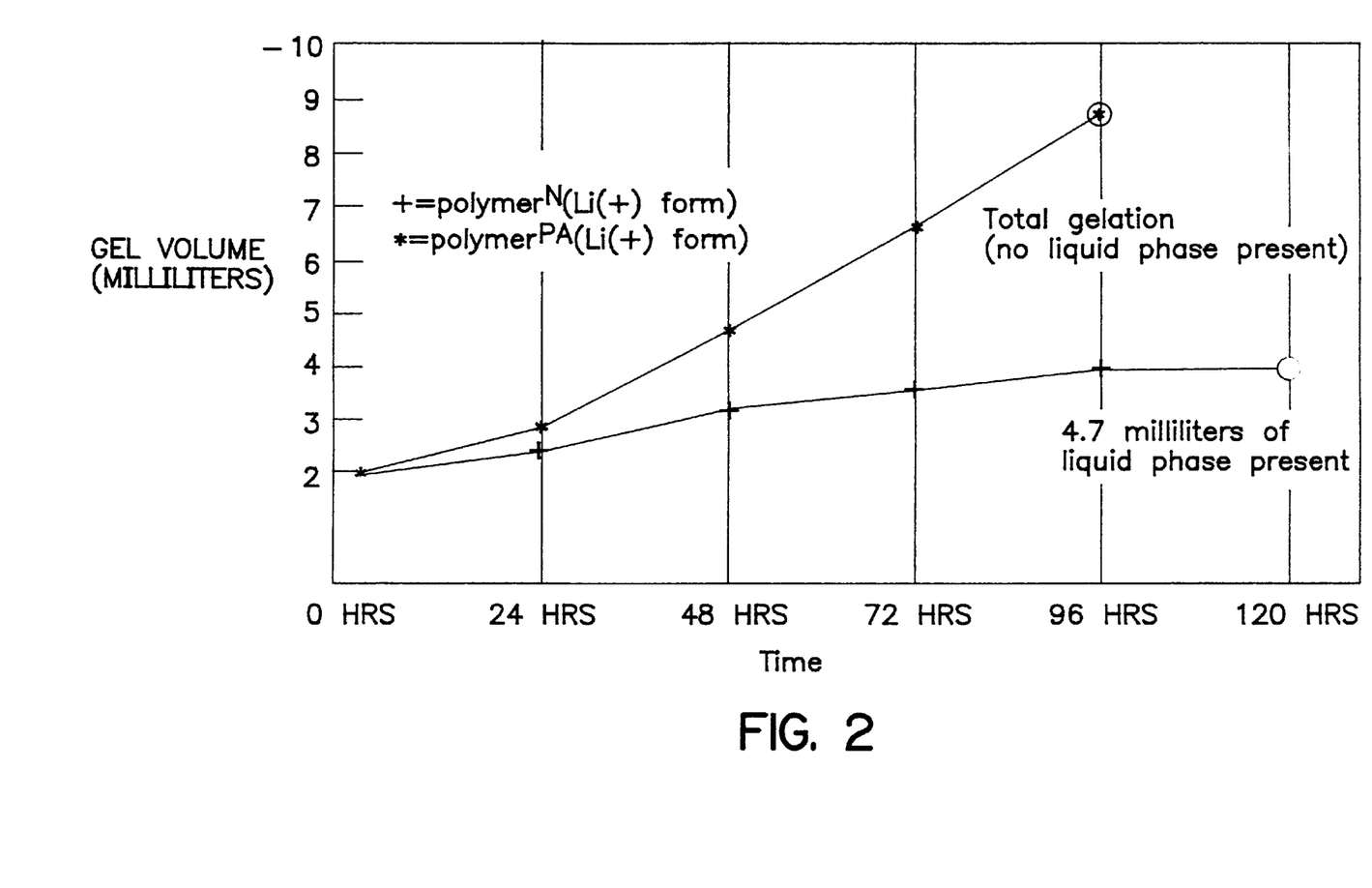
FIG. 2 is an experiment in aqueous lithium chloride.
Figure 3:
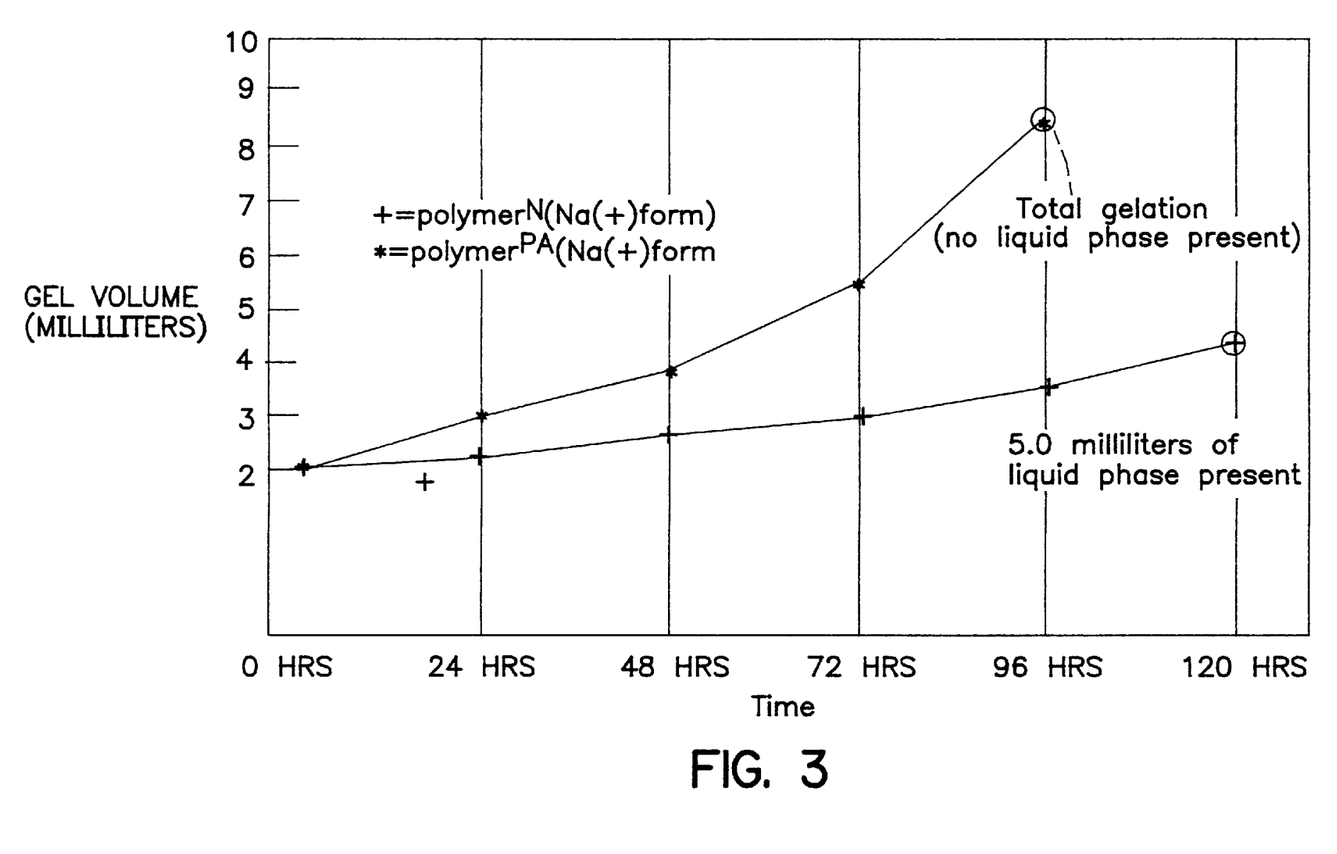
FIG. 3 is an experiment in aqueous sodium chloride.
Figure 4:
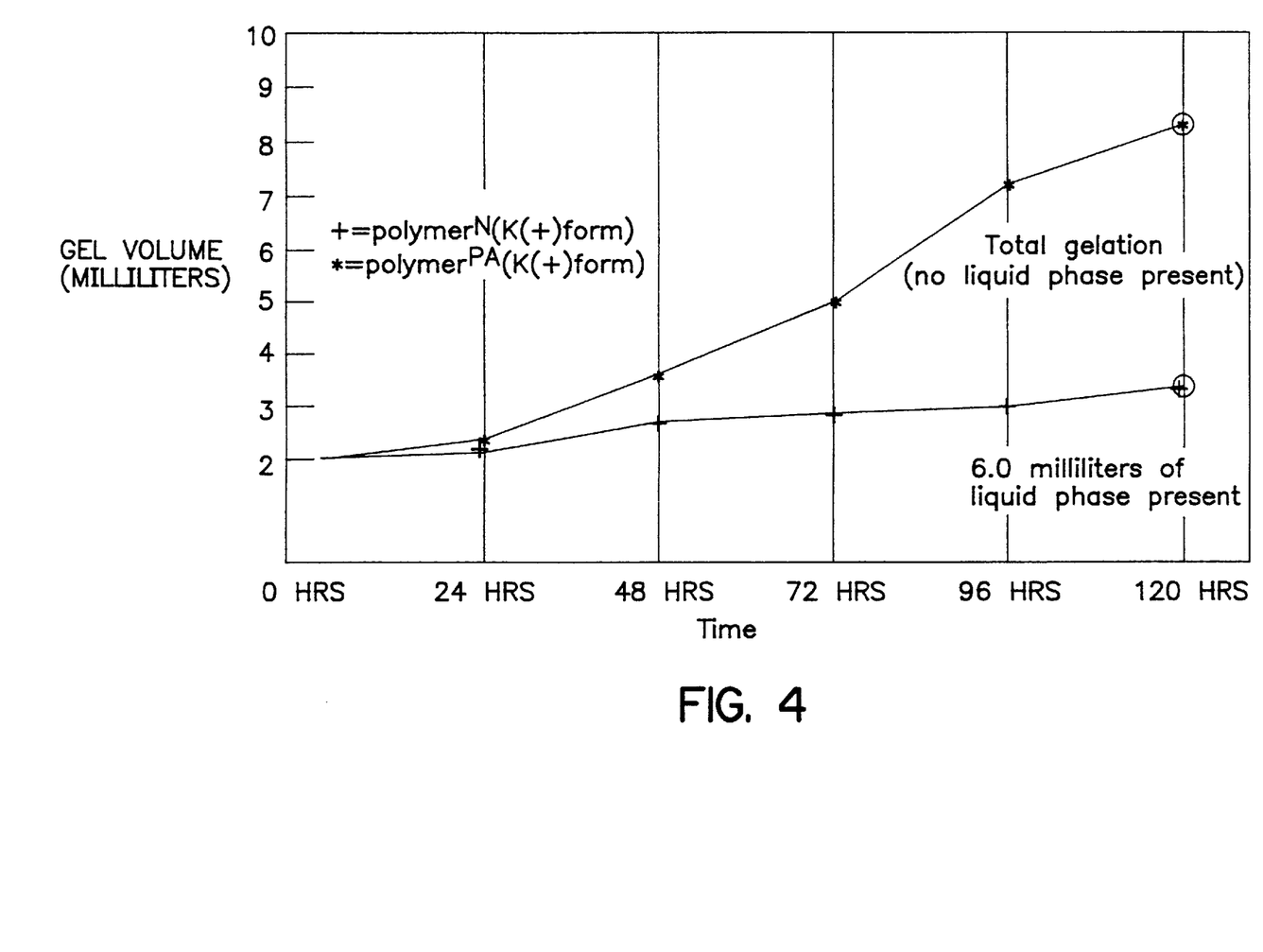
FIG. 4 is an experiment in aqueous potassium chloride.
Figure 5:
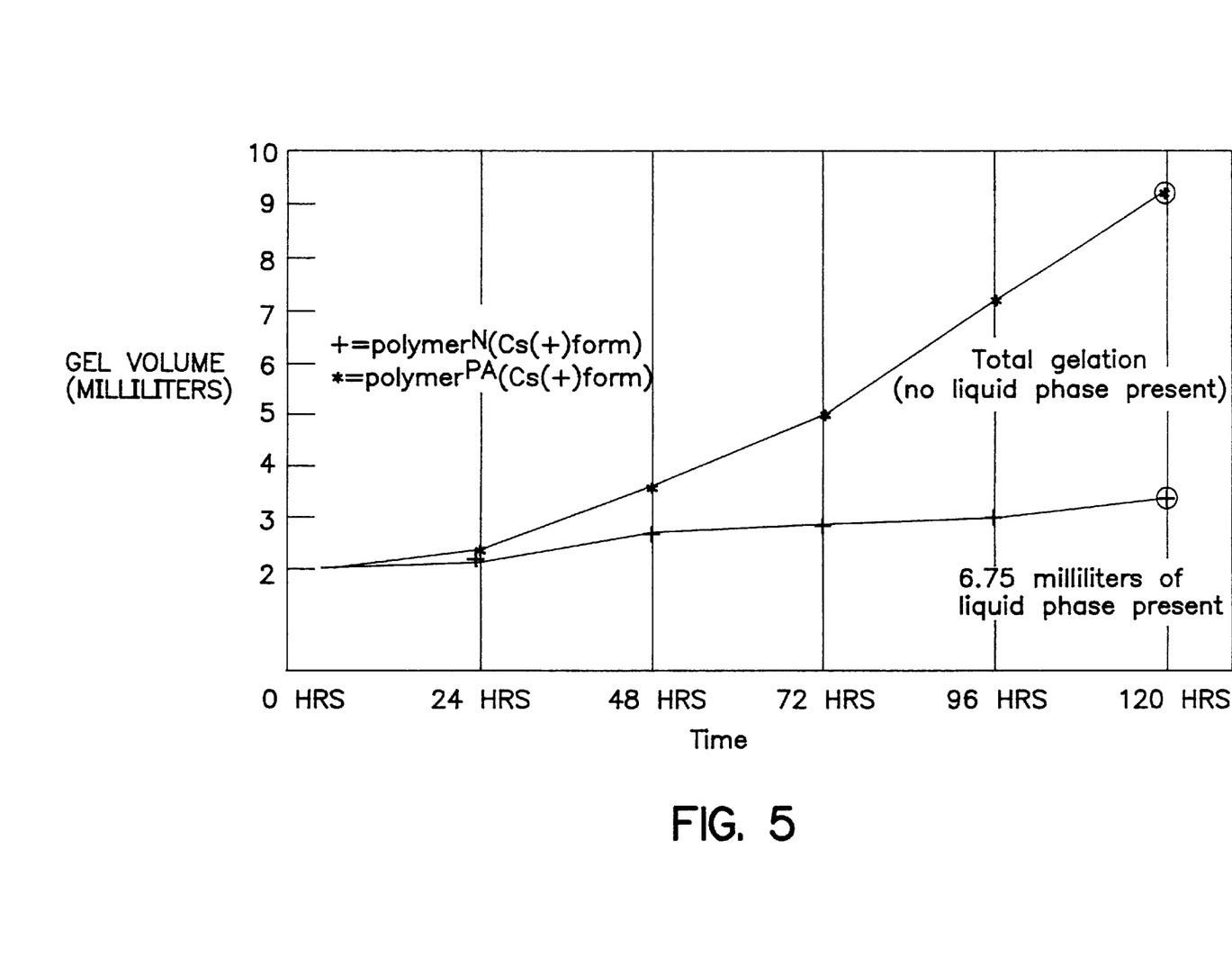
FIG. 5 is an experiment in aqueous caesium chloride.

The increase in gel volume in the various media is depicted graphically (FIGS. 1–5). Gel expansion is much more evident in suspension of polymer PA than in suspensions of polymer N regardless of the counterion that is present, or on the incubation time. Total conversion of polymer PA into a non-pipetable viscous gel occurred after a period of 72 hours in pure water; after 96 hours in 0.1 M lithium chloride and 0.1 M sodium chloride respectively, and after 120 hours in 0.1 M potassium chloride and 0.1 M cesium chloride respectively. In contrast suspensions of polymer N showed a lesser tendency towards gelation as evidenced by less gel formation. After 120 hours of incubation, a substantial quantity of liquid phase was still present in all of the preparations of polymer N. With regard to the nature of the counterion in the suspending media, the volume recovery decreased in the order $Cs^+>K^+>Na^+>Li^+>H^+$.

All of the suspensions of polymer N were pipetable after the 120 hour, 45° C., incubation period. Under these conditions, polymer PA had undergone a total transition into a viscous gel state, and were not amenable for further testing. Incubated polymer N suspensions were tested for protein binding capacity and the results compared with the non-heated counterpart.

EXAMPLE 7

The effect of prolonged heating on the protein binding capacity of polymer N was determined. After heating 1.0% w/w suspensions in water and in the presence of aqueous solutions of the chloride salts of the Group 1 element at 45° C. for 120 hours, the polymer was tested for protein binding. One ml volumes of the respective polymer suspension was added to 1.0 ml volumes of bovine serum albumin (BSA) 33.0 mg/ml in phosphate buffered saline pH 7.3. The contents was vortexed, allowed to sit at room temperature for 10 minutes and then centrifuged. The supernatants were removed and analyzed for protein. The results are reported below for polymer PN only.

TABLE 2

| Suspending Media | % Protein Removed Prior to Incubation | % Protein Removed After Incubation for 120 Hours at 45° C. |
| --- | --- | --- |
| H₂O | 98.7 | 98.0 |
| 0.1 M LiCl | 99.1 | 98.7 |
| 0.1 M NaCl | 98.7 | 98.2 |
| 0.1 M KCl | 98.5 | 99.1 |
| 0.1 M CsCl | 98.2 | 98.9 |

The data indicated that incubation at 45° C. for 120 hours had no detectable effect on the protein binding capacity of polymer N.

I claim:

1. A water insoluble cross-linked polycarboxylic acid containing material obtained by cross-linking a polymer of the formula:

wherein
R is hydrogen or lower alkylene or lower alkoxy of 1–4 carbon atoms, or phenyl,
x and y are integers,
with an alpha, omega diamino alkane of the formula:

wherein
z is an integer of 1–6,
p is 0 or an integer up to z-1,
m is 0 or an integer up to z,
w is an integer of 2–12,
and hydrolyzing the unreacted anhydride groups.

2. The material of claim 1 wherein w=6, z=3–6 and the ratio of the diaminoalkane to the poly (alkylene maleic anhydride) (I) is between about $1\times10^{-5}$ to $1\times10^{-3}$ moles of diamino-alkane to 1.0 grams of polymer.

3. The material of claim 1 wherein x and y are between 7 and 10,000.

4. The product obtained by reacting the product of claim 1 with aqueous alkali.

5. A water insoluble cross-linked polycarboxylic acid having the formula:

wherein
R is hydrogen or lower alkylene or lower alkoxy of 1–4 carbon atoms, or phenyl,
x and y are integers, z is an integer of 1–6,
p is 0 or an integer up to z–1,
m is 0 or an integer up to z,
w is an integer from 2–12.

6. The acid of claim 5 wherein w=6, z=3–6 and the ratio of the diaminoalkane to the poly (alkylene maleic anhydride) (I) is between about $1 \times 10^{-5}$ to $1 \times 10^{-3}$ moles of diamino-alkane to 1.0 grams of polymer.

7. The acid of claim 5 wherein x and y are between 7 and 10,000.

8. The acid of claim 6 wherein R is methoxy and m=1 or 0.

9. A method of making a water insoluble cross-linked polyhydroxy polycarboxylic acid containing material of claim 5 which comprises cross-linking a polymer of the formula:

(I)

wherein
R is hydrogen or lower alkylene or lower alkoxy of 1–4 carbon atoms, or phenyl,
x and y are integers,
w is an integer from 2–12
with an alpha, omega diaminoalkane, of the formula:

(II)

wherein
z is an integer of 1–4,
p is 0 or an integer up to z–1,
m is 0 or an integer up to z,
and hydrolyzing the unreacted anhydride groups.

10. The method of claim 9 wherein w=6, z=3–6 and the ratio of the diaminoalkane to the poly (alkylene maleic anhydride) (I) is between about $1 \times 10^{-5}$ to $1 \times 10^{-3}$ moles of diaminoalkane to 1.0 grams of polymer.

11. The method of claim 10 wherein x and y are between 7 and 10,000.

12. The method of claim 10 wherein R is methoxy and m=1 or 0.

13. A method of precipitating protein from an aqueous medium containing the same which comprises adding thereto an effective amount of a polycarboxylic acid containing material of claim 5 to provide a protein/polycarboxylic acid matrix.

14. The method of precipitating protein from an aqueous medium containing the same which comprises adding thereto an effective amount of a polycarboxylic acid of claim 8 to provide a protein/polycarboxylic acid matrix.

15. The method of claim 13 wherein the amount of polycarboxylic acid containing material utilized, by weight, is at least equal to the amount of protein contained in the aqueous medium containing same.

16. The method of claim 14 wherein the amount of polycarboxylic acid utilized, by weight, is at least equal to the amount of protein contained in the aqueous medium containing same.

17. The method of claim 13 wherein the polycarboxylic acid containing material is utilized in an aqueous medium.

18. The method of claim 14 wherein the polycarboxylic acid is utilized in an aqueous medium.

19. The method of claim 17 wherein the concentrations by weight of protein and of polycarboxylic acid containing material in their respective aqueous media have a ratio of between about 3:1 to about 1:3.

20. The method of claim 18 wherein the concentrations by weight of protein and of polycarboxylic acid in their respective aqueous media have a ratio of between about 3:1 to about 1:3.

21. The method of claim 19 wherein the concentrations by weight of protein and of polycarboxylic acid containing material in their respective aqueous media are substantially equal.

22. The method of claim 20 wherein the concentrations by weight of protein and of polycarboxylic acid in their respective aqueous media are substantially equal.

23. The method of claim 18 wherein R is methoxy and m=0, and the pH of the polycarboxylic acid containing medium is between about 3 to about 6.2 to provide a medium after mixture of the polycarboxylic acid and protein which does not exceed about pH 6.5.

24. The method of claim 18 wherein R is methoxy and m=1, and the pH of the polyhydroxy polycarboxylic aid containing medium is between about 5.5 to about 7.5 to provide a medium after mixture of the polycarboxylic acid and protein which does not exceed about pH 7.5.

25. The method of claim 13 which comprises recovering the matrix as a pellet by centrifugation.

26. The method of claim 14 which comprises recovering the matrix as a pellet by centrifugation.

27. The method of separating the protein from the matrix of claim 25 without denaturing said protein which comprises treating said matrix with a buffer at about pH 7.0 to about 8.5.

28. A method of separating the protein from the matrix of claim 26 without denaturing said protein which comprises treating said matrix with a buffer at about pH 7.0 to about 8.5.

29. The method of claim 27 which comprises treating the matrix with about 1 to about 5 volumes of buffer, at about pH 7.0 to about 8.5, per volume of pellet of the matrix.

30. The method of claim 28 which comprises treating the matrix with about 1 to about 5 volumes of buffer, at about pH 7.0 to about 8.5, per volume of pellet of the matrix.

31. The method of claim 29 wherein the buffer is a Tris buffer.

32. The method of claim 30 wherein the buffer is a Tris buffer.

33. A method of separating the polycarboxylic acid containing material from the matrix of claim 13 to recover the same which comprises treating said matrix with an aqueous solution of sodium lauryl sulfate.

34. A method of separating the polycarboxylic acid containing material from the matrix of claim 14 to recover the same which comprises treating said matrix with an aqueous solution of sodium lauryl sulfate.

35. The method of claim 33 which comprises the further step of centrifuging said matrix which has been treated with sodium lauryl sulfate solution and recovering the polycarboxylic acid from the residual pellet thereof.

36. The method of claim 34 which comprises the further step of centrifuging said matrix which has been treated with sodium lauryl sulfate solution and recovering the polycarboxylic acid from the residual pellet thereof.

37. The method of claim 33 which comprises treating the matrix with about 1 to about 3 volumes of sodium lauryl sulfate of a concentration of between about 0.5 and about 2% w/w per volume of matrix residual pellet.

38. The method of claim 36 wherein there are used about 1 to about 3 volumes of sodium lauryl sulfate of a concentration of between about 0.5 and about 2% w/w per volume of matrix residual pellet.

39. The method of claim 38 which comprises the further step of washing the said recovered polycarboxylic acid residue in deionized water and resuspending same in deionized water.

40. The method of claim 39 wherein said deionized water has a pH of 4.0–4.5.

41. The method of claim 13 wherein the aqueous medium containing said protein further contains nucleic acid.

42. The method of claim 14 wherein the aqueous medium containing said protein further contains nucleic acid.

43. The method of claim 41 wherein the source of nucleic acid is a cell lysate suspended in aqueous guanidinium thiocyanate.

44. The method of claim 42 wherein the source of nucleic acid is a cell lysate suspended in aqueous guanidinium thiocyanate.

45. The method of claim 41 wherein the source of nucleic acid is a cell lysate suspended in aqueous sodium dodecyl sulfate.

46. The method of claim 42 wherein the source of nucleic acid is a cell lysate suspended in aqueous sodium dodecyl sulfate.

47. The stabilized aqueous solution of an acid of claim 5 comprising between 0.01 and 10% w/w of said acid in between 0.05 and 0.5 M of an alkali metal salt solution.

48. The solution of an acid of claim 8 comprising between 0.01 and 10% w/w of said acid in between 0.05 and 0.5 M of an alkali metal salt solution.

49. The solution according to claim 48 wherein the alkali metal is K or Cs and the anion of said salt is Cl.

50. The solution according to claim 49 wherein there is dispersed 1 to 3% w/w of the said acid in 0.1–0.3 M of aqueous CsCl.

* * * * *

UNITED STATES PATENT AND TRADEMARK OFFICE
CERTIFICATE OF CORRECTION

PATENT NO. : 5,976,382
DATED : November 2, 1999
INVENTOR(S) : John Krupey

It is certified that error appears in the above-identified patent and that said Letters Patent is hereby corrected as shown below:

Title page, item [54] and Column 1:
Delete, "REMOVAL OF PROTEINS FROM AQUEUOS MEDIA BY PRECIPITATION", insert in place thereof -- REMOVAL OF PROTEINS FROM AQUEOUS MEDIA BY PRECIPITATION --

Signed and Sealed this

Twenty-third Day of May, 2000

Attest:

Q. TODD DICKINSON

*Attesting Officer*     *Director of Patents and Trademarks*